US00PP20593P2

(12) United States Plant Patent
Tonies

(10) Patent No.: US PP20,593 P2
(45) Date of Patent: Dec. 22, 2009

(54) ***PHLOX* PLANT NAMED 'DITOSMEL'**

(50) Latin Name: *Phlox paniculata*
Varietal Denomination: Ditosmel

(75) Inventor: Hubertus Josephus Tonies, Noordwijkerhout (NL)

(73) Assignee: Ditoplant Export B.V., Noordwijkerhout (NL)

( * ) Notice: Subject to any disclaimer, the term of this patent is extended or adjusted under 35 U.S.C. 154(b) by 0 days.

(21) Appl. No.: 12/286,049

(22) Filed: Sep. 26, 2008

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent L Bell
(74) *Attorney, Agent, or Firm*—C. A. Whealy

(57) ABSTRACT

A new and distinct cultivar of *Phlox* plant named 'Ditosmel', characterized by its upright and mounding plant habit; freely branching and flowering habit; long flowering period; dark pink-colored flowers; and good garden performance.

1 Drawing Sheet

Botanical designation: *Phlox paniculata.*
Cultivar denomination: 'Ditosmel'.

BACKGROUND OF THE INVENTION

The present invention relates to a new and distinct cultivar of *Phlox,* botanically known as *Phlox paniculata* and hereinafter referred to by the name 'Ditosmel'.

The new *Phlox* plant is a product of a planned breeding program conducted by the Inventor in Noordwijkerhout, The Netherlands. The objective of the breeding program is to create new compact *Phlox* cultivars with attractive leaf and flower coloration.

The new *Phlox* plant originated from an open-pollination in Noordwijkerhout, The Netherlands in July, 2004, of *Phlox paniculata* 'Uspech', not patented, as the female, or seed parent with an unknown selection of *Phlox paniculata*, as the male, or pollen, parent. The new *Phlox* was discovered and selected by the Inventor as a single flowering plant from within the progeny of the stated open-pollination in a controlled outdoor nursery environment in Noordwijkerhout, The Netherlands in July, 2005.

Asexual reproduction of the new *Phlox* plant by cuttings in a controlled greenhouse environment in Noordwijkerhout, The Netherlands since January, 2006, has shown that the unique features of this new *Phlox* plant are stable and reproduced true to type in successive generations.

SUMMARY OF THE INVENTION

Plants of the new *Phlox* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Ditosmel'. These characteristics in combination distinguish 'Ditosmel' as a new and distinct cultivar of *Phlox:*

1. Upright and mounding plant habit.
2. Freely branching and flowering habit.
3. Long flowering period.

4. Dark pink-colored flowers.
5. Good garden performance.

Plants of the new *Phlox* differ from plants of the female parent, 'Uspech', in the following characteristics:

1. Plants of the new *Phlox* are more upright and sturdier than plants of 'Uspech'.
2. Plants of the new *Phlox* are more freely branching than plants of 'Uspech'.
3. Inflorescences of plants of the new *Phlox* are more uniform and fuller than inflorescences of plants of 'Uspech'.

Plants of the new *Phlox* can also be compared to plants of *Phlox paniculata* 'Junior Dream', disclosed in U.S. Plant Pat. No. 16,059. In side-by-side comparisons conducted in Noordwijkerhout, The Netherlands, plants of the new *Phlox* and 'Junior Dream' differed in the following characteristics:

1. Plants of the new *Phlox* were stronger and sturdier than plants of 'Junior Dream'.
2. Plants of the new *Phlox* were more freely branching than plants of 'Junior Dream'.
3. Inflorescences of plants of the new *Phlox* were more uniform and fuller than inflorescences of plants of 'Junior Dream'.

BRIEF DESCRIPTION OF THE PHOTOGRAPHS

The accompanying colored photographs illustrate the overall appearance of the new *Phlox*, showing the colors as true as it is reasonably possible to obtain in colored reproductions of this type. Colors in the photographs may differ slightly from the color values cited in the detailed botanical description which accurately describe the colors of the new *Phlox.*

The photograph at the bottom of the sheet comprises a side perspective view of a typical flowering plant of 'Ditosmel' grown in a container.

The photograph at the top of the sheet is a close-up view of typical flowers of 'Ditosmel'.

DETAILED BOTANICAL DESCRIPTION

The aforementioned photographs and following observations, measurements and values describe plants grown in Lancaster, Pa., under commercial practice during the summer in 20-cm containers in a polyethylene-covered greenhouse with day temperatures ranging from 13° C. to 32° C. and night temperatures ranging from 13° C. to 30° C. Plants had been growing for 17 weeks when the photographs and description were taken. In the following description, color references are made to The Royal Horticultural Society Colour Chart, 2001 Edition, except where general terms of ordinary dictionary significance are used.

Botanical classification: *Phlox paniculata* 'Ditosmel'.

Parentage:

*Female, or seed, parent.*—*Phlox paniculata* 'Uspech', not patented.

*Male, or pollen, parent.*—Unknown selection of *Phlox paniculata*, not patented.

Propagation:

*Type.*—By cuttings.

*Time to initiate roots.*—About three weeks at 20° C.

*Time to produce a rooted young plant.*—About 25 days at 20° C.

*Root description.*—Fibrous; grayed tan in color.

*Rooting habit.*—Freely branching; moderately dense.

Plant description:

*Plant form/habit.*—Upright and mounding plant habit; vigorous growth habit. Freely branching habit with about 22 lateral branches per plant; pinching enhances branching. Uniform and full inflorescences.

*Plant height.*—About 42 cm.

*Plant width (spread).*—About 37 cm.

*Lateral branches.*—Length: About 32 cm. Diameter: About 4.5 mm. Internode length: About 3 cm. Strength: Strong. Texture: Smooth, glabrous. Color: Close to 146A tinted with close to 185A.

Foliage description:

*Arrangement.*—Opposite, simple; sessile, clasping.

*Length.*—About 9.2 cm.

*Width.*—About 2.7 cm.

*Shape.*—Narrowly elliptic.

*Apex.*—Acute.

*Base.*—Attenuate.

*Margin.*—Entire.

*Texture, upper and lower surfaces.*—Smooth, glabrous.

*Venation pattern.*—Pinnate, reticulate.

*Color.*—Developing leaves, upper and lower surfaces: Close to 146B. Fully expanded leaves, upper surface: Close to 147A; venation, close to 146B. Fully expanded leaves, lower surface: Close to 147B; venation, close to 146C.

Flower description:

*Flower type/habit.*—Single rotate flowers arranged in terminal compound cymes; flowers face mostly upright or outwardly. Cymes rounded and hemispherical in shape. Freely flowering habit with about 175 flowers developing per inflorescence.

*Fragrance.*—Slightly fragrant; sweet, pleasant.

*Natural flowering season.*—Continuously flowering during July in Pennsylvania.

*Postproduction longevity.*—Flowers last about five to seven days on the plant; flowers not persistent.

*Flower buds.*—Height: About 2.2 cm. Diameter: About 4 mm. Shape: Clavate. Color: Close to 65A .

*Inflorescence height.*—About 8.5 cm.

*Inflorescence diameter.*—About 9.8 cm.

*Flower diameter.*—About 2.5 cm.

*Flower depth.*—About 1.8 cm.

*Throat diameter.*—About 3 mm.

*Tube length.*—About 1.4 cm.

*Tube diameter, base.*—About 2 mm.

*Petals.*—Quantity per flower: Typically five in a single whorl; petals fused at the base into a narrow tube. Length from throat: About 1.2 cm. Lobe width: About 1.1 cm. Lobe shape: Roughly spatulate. Apex: Rounded. Margin: Entire. Texture, upper and lower surfaces and throat: Smooth, glabrous. Texture, tube: Sparsely pubescent. Color: Developing petals, upper surface: Close to 65A. Developing petals, lower surface: Close to 65B to 65C. Fully expanded petals, upper surface: Close to 75B; towards the base, close to N74B; venation, close to 75B. With development, color becoming closer to slightly lighter than 75C. Fully expanded petals, lower surface: Close to 75C; venation, close to 75C. Throat: Close to N77D; towards the base, close to 69D; venation, close to N77D. Tube: Close to N77B; venation, close to N77B.

*Sepals.*—Quantity per flower: Typically five in a single whorl, fused towards the base. Length: About 4 mm. Width: Less than 1 mm. Shape: Lanceolate. Apex: Acuminate. Margin: Entire. Texture, upper and lower surfaces: Smooth, glabrous. Color, developing and fully expanded sepals, upper surface: Close to 146A. Color, developing and fully expanded sepals, lower surface: Close to 147C.

*Peduncles.*—Length: About 3.7 cm. Diameter: About 2.5 mm. Strength: Strong. Texture: Pubescent. Color: Close to 146C with flecks, close to 185A.

*Pedicels.*—Length: About 5 mm. Diameter: Less than 1 mm. Strength: Strong. Texture: Pubescent. Color: Close to 146A.

*Reproductive organs.*—Stamens: Quantity per flower: Typically five. Anther shape: Narrowly oblong. Anther length: About 2 mm. Anther color: Close to 160C. Pollen amount: Scarce. Pollen color: Close to 155A. Pistils: Quantity per flower: One. Pistil length: About 1.7 cm. Stigma shape: Three-parted. Stigma color: Close to 160C. Style length: About 1.4 cm. Style color: Close to 145C. Ovary color: Close to 146C.

*Seed/fruit.*—Seed and fruit development have not been observed.

Disease/pest resistance: Plants of the *Phlox* have not been observed to be resistant to pathogens and pests common to *Phlox*.

Garden performance: Plants of the new *Phlox* have been observed to have good garden performance and tolerate rain, wind and temperatures ranging from about 0° C. to about 35° C.

It is claimed:

1. A new and distinct *Phlox* plant named 'Ditosmel' as illustrated and described.

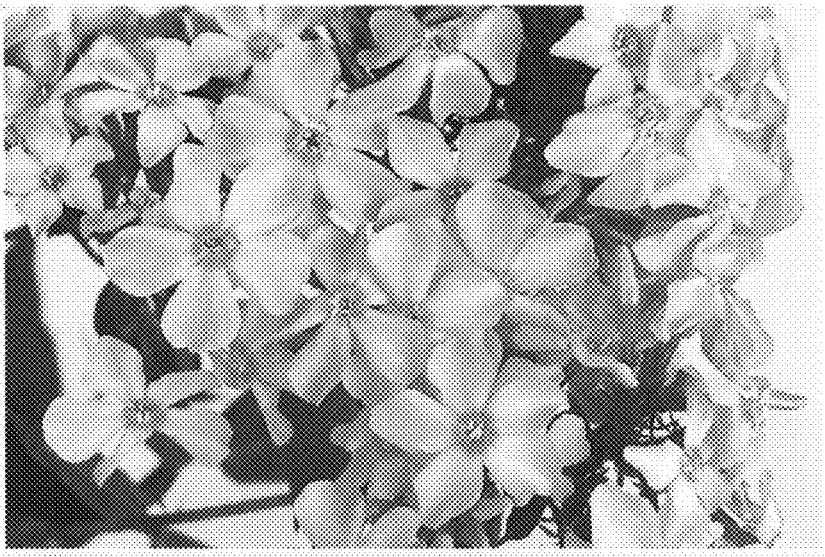
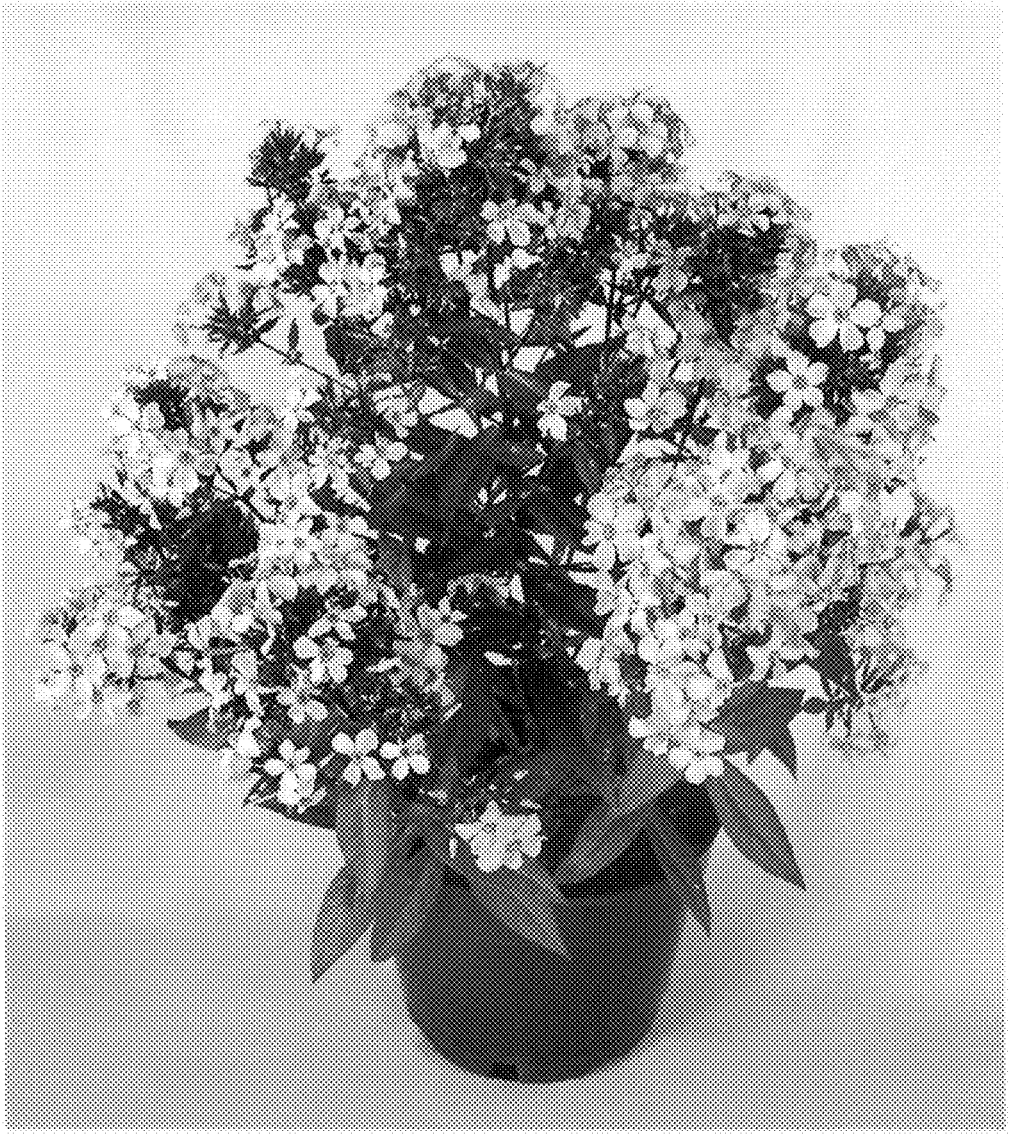

* * * * *